United States Patent [19]

Fowler et al.

[11] Patent Number: 4,913,891

[45] Date of Patent: Apr. 3, 1990

[54] POSITRON EMITTER LABELED ENZYME INHIBITORS

[75] Inventors: Joanna S. Fowler, Bellport; Robert R. MacGregor, Sag Harbor; Alfred P. Wolf, Setauket, all of N.Y.; Bengt Langstrom, Upsala, Sweden

[73] Assignee: The United States of America as represented by the United States Department of Energy, Washington, D.C.

[21] Appl. No.: 52,921

[22] Filed: May 22, 1987

Related U.S. Application Data

[63] Continuation-in-part of Ser. No. 853,119, Apr. 17, 1986, abandoned.

[51] Int. Cl.$^4$ .................. A61K 49/02; A61K 31/135; C07C 93/06; C07C 87/28
[52] U.S. Cl. ........................................... 424/11; 424/9; 514/651; 514/654; 564/353; 564/381; 564/382
[58] Field of Search ..................... 424/1.1, 9; 514/651, 514/654; 564/353, 381, 382

[56] References Cited

PUBLICATIONS

Fowler, J. S., "Synthesis of $^{14}$C-Labeled Suicide Inactivators of MAO," *J. Lab. Cmpds. and Radio.*, vol. 14, 3, 435–437, 1978.

Ishiwata et al., "Biodistribution of a Positron-Emitting Suicide Inactivator of MAO," *J. Nucl. Med.*, 26, 630–636, 1985.

MacGregor et al., *Biochemical Pharmacology*, vol. 34, No. 17, pp. 3207–3210 (1985).

Inoue et al., *J. Neurochemistry*, vol. 44, No. 1, pp. 210–216 (1985).

Inoue et al., *Japanese J. Nuclear Medicine*, vol. 21, No. 6, pp. 671–678.

*Primary Examiner*—John S. Maples
*Attorney, Agent, or Firm*—Margaret C. Bogosian; James W. Weinberger; Judson R. Hightower

[57] ABSTRACT

This invention involves a new strategy for imaging and mapping enzyme activity in the living human and animal body using positron emitter-labeled suicide enzyme inactivators or inhibitors which become covalently bound to the enzyme as a result of enzymatic catalysis. Two such suicide inactivators for monoamine oxidase have been labeled with carbon-11 and used to map the enzyme subtypes in the living human and animal body using PET. By using positron emission tomography to image the distribution of radioactivity produced by the body penetrating radiation emitted by carbon-11, a map of functionally active monoamine oxidase activity is obtained. Clorgyline and L-deprenyl are suicide enzyme inhibitors and irreversibly inhibit monoamine oxidase. When these inhibitors are labeled with carbon-11 they provide selective probes for monoamine oxidase localization and reactivity in vivo using positron emission tomography.

8 Claims, 2 Drawing Sheets

POSITRON EMITTER LABELED ENZYME INHIBITORS

The U.S. Government has rights in this invention pursuant to Contract Number DE-AC02-76CH00016, between the U.S. Department of Energy and Associated Universities Inc.

RELATED APPLICATIONS

The instant application is a continuation-in-part application of co-pending U.S. patent application Ser. No. 853,119 filed Apr. 17, 1986 and now abandoned.

FIELD OF INVENTION

This invention involves a new strategy for imaging and mapping the regional distribution of enzymes in the living body by using positron emitter-labeled suicide enzyme inhibitors which bind irreversibly to the enzyme through catalysis, thereby labeling said enzyme. Carbon-11 is the radiolabel of choice because it is a positron emitter with a half-life of 20.4 minutes. By using positron emission tomography to image the distribution of the radioactivity produced by the body penetrating radiation emitted by the radiolabel, a map of functionally active enzyme activity is obtained. One preferred application of the instant invention is to map the activity of functionally active monoamine oxidase.

SUMMARY OF THE INVENTION

Because of the pivotal role played by enzymes in virtually all biochemical transformations, the identification of abnormalities associated with enzyme activity and distribution assists in understanding disease at the molecular level and in diagnosing such disease and developing more effective treatment for such disease. For example, alterations in the enzyme monoamine oxidase have been implicated in a number of mental disorders and diseases. Two types of monoamine oxidase (A and B) have been identified by their substrate selectivity as well as by their selective inhibition by the propargyl amines clorgyline and L-deprenyl. Clorgyline and L-deprenyl are referred to as suicide enzyme inhibitors and irreversibly inhibit monoamine oxidase by forming covalent adducts between the flavine of monoamine oxidase and the propynyl groups. These inhibitors, which are substrates for monoamine oxidase A and B, respectively, deactivate the enzyme by becoming covalently or irreversibly attached to the active site of the enzyme after catalysis. Therefore, when these inhibitors are labeled with the positron emitter carbon-11 at the N-methyl carbon, they provide selective probes for monoamine oxidase localization and reactivity in vivo using positron emission tomography. By labeling these two inhibitors with carbon-11, it is possible to label selectively each monoamine oxidase type in vivo and to determine quantitatively the patterns of distribution of the enzyme using positron emission tomography. Carbon-11 labeled clorgyline and L-deprenyl are prepared by the alkylation of the corresponding desmethyl amines with a [$^{11}$C] methyl halide, preferably [$^{11}$C] methyl iodide.

The in-vivo labeling of other enzymes such as ornithine decarboxylase, dopa decarboxylase, dopamine B-hydroxylase, alcohol dehydrogenase and other enzymes is possible by labeling known suicide enzyme inactivators of these enzymes with positron emitting isotopes. Such labeling will provide a general approach to selectively mapping these different enzymes in the living body of humans and animals.

DETAILED DESCRIPTION OF THE INVENTION

Figure 1:
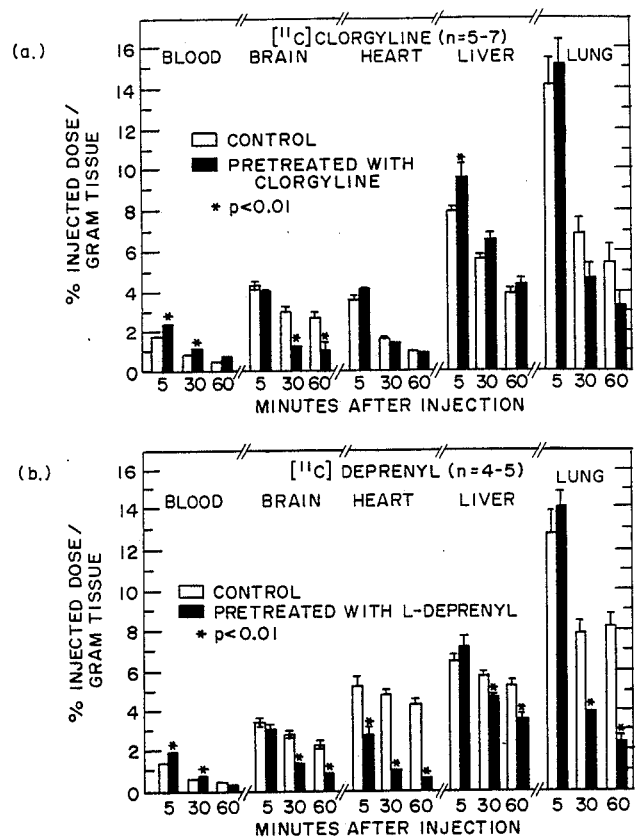
FIG. 1 shows the time course of distribution of radioactivity in mice (average±S.E.M. of 4 to 7 animals) following administration of (a) [$^{11}$C] clorgyline or (b) [$^{11}$C]-L-deprenyl in control and pretreated animals. Asterisks (*) indicate values which differ significantly from control (p<0.01).

The carbon-11 labeled compounds used in the imaging and mapping procedures of the present invention are prepared by the alkylation of the corresponding desmethyl amines as follows:

(1) Preparation of [$^{11}$C] clorgyline:

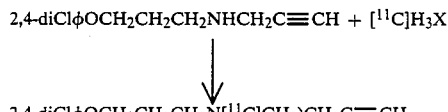

wherein X is selected from the group consisting of chlorine, bromine and iodine.

(2) Preparation of [$^{11}$C]-L-deprenyl:

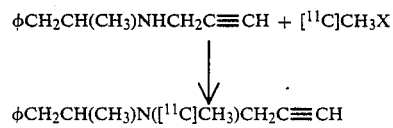

wherein X is selected from the group consisting of chlorine, bromine and iodine.

• Synthesis time is about 30–45 minutes, with the optimum runs taking about 35 minutes, with a radiochemical yield at end of bombardment (EOB) of about 20–40% and a specific activity of about 0.8–2.0C:μmole (EOB). Differences in tissue distribution between control and [$^{11}$C] clorgyline or [$^{11}$C]-L-deprenyl in pretreated mice demonstrate specific uptake and retention of each of the labeled inhibitors (tracers) by organs known to contain the specific monoamine oxidase type.

Clorgyline and L-deprenyl labeled with the positron emitter C-11 have been synthesized from the corresponding desmethyl compounds by alkylation with [$^{11}$C]methyl iodide, the production of which has been described by Dannals et al., J. Nucl. Med., 26, 126 (1985). The [$^{11}$C] labeled monoamine oxidase inhibitors were obtained in good yield (25–40% EOB) in a reasonable synthesis time (35 min) and in a state of high chemical and radiochemical purity through the use of preparative high performance liquid chromatography (HPLC). Yields were improved significantly by the use of an excess of the free base of the amine, rather than the hydrochloride salt and an organic base. In addition the use of a solvent mixture of DMF:DMSO (4:1) in the methylation step increased the radiochemical yield.

In the preparative reactions a two fold excess of amine over alkyl bromide was employed in an attempt to minimize dialkylation of the amine. In addition to the methods described below, clorgyline and deprenyl were synthesized on a preparative scale by the reactions of the nor compounds with methyl iodide.

Positron emission tomography is useful to determine local cerebral metabolic rates and neurotransmitter receptor distributions in vivo, using appropriate radioligands labeled with positron-emitting nuclides. This in vivo technique has been extended in the present invention to the selective mapping of the distribution of monoamine oxidase types A and B, an enzyme important in the etiology, diagnosis, and treatment of mental diseases. To perform this mapping, clorgyline and L-deprenyl, selective irreversible inhibitors of monoamine oxidase types A and B, respectively, are radiolabeled with carbon-11, a positron emitting nuclide, to image the monoamine oxidase activity in the intact laboratory animal or human subject.

Comparison of the in vivo disposition of these two radioligands between control mice and mice pretreated with 10 mg/kg i.p. of unlabeled compound demonstrated selective distribution and retention in organs known to contain high concentrations of the respective monoamine oxidase type. [$^{11}$C]Clorgyline distributed specifically to brain, whereas [$^{11}$C]-L-deprenyl distributed to brain, heart, liver, and lung tissues. Cross pretreatment studies showed no effect of clorgyline on [$^{11}$C]-L-deprenyl distribution and vice versa.

Influx rate constants and integrated plasma activity after injection of the two C-11 labeled monoamine oxidase inhibitors in several human subjects is shown in Table 1.

Successful positron emission tomography studies in baboons utilizing a double injection paradigm with an intervening high dose of unlabeled compound demonstrated the feasibility of this approach for selective imaging of monoamine oxidase types in the whole intact bodies of larger experimental animals and humans. Pretreatment of the baboon with L-deprenyl reduced the radioactivity due to [$^{11}$C]-L-deprenyl in some brain regions by as much as 80 percent, indicating that positron emission tomography may be used effectively to map enzyme distributions in vivo.

Monoamine oxidase (EC 1.4.3.4, amine: $O_2$ oxidoreductase, MAO) which catalyzes the oxidative deamination of a variety of monoamines, has been subdivided, on the basis of substrate and inhibitor selectivity, into two types: MAO-A and MAO-B. The A form selectively oxidizes 5-hydroxytryptamine and is selectively and irreversibly inhibited by clorgyline. The B form selectively oxidizes benzylamine and is inhibited by L-deprenyl.

One embodiment of the present invention is the use of the carbon-11 positron emitter labeled radiotracers [$^{11}$C]clorgyline and [$^{11}$C]-L-deprenyl to probe functional MAO activity in vivo. One significant advantage of this approach is the potential of selectively assaying MAO A or B using tracers whose inhibitory profiles are well characterized and whose use has provided the basis for the development of an extensive data base on MAO A and B.

EXAMPLE 1

Materials and Methods

Propargyl amine, N-methyl propargyl amine, propargyl bromide (80% in toluene) and 2,4-dichlorophenol were purchased from Aldrich. L-Amphetamine was purchased from Sigma, D-amphetamine was purchased from K and K Laboratories and 1,3-dibromopropane from Eastman.

Amines were converted to their hydrochloride salts by the gradual addition of a solution of dry HCl in ether to an ethereal solution of the amine, followed by centrifugation. NMR spectra were run on a Bruker 300 MHz instrument using $CDCl_3$ as a solvent and TMS as an internal standard. Optical rotations were run on a Rudolf polarimeter.

TABLE 1

Influx rate constants ($K_1$) for four normal volunteers (studies 1 to 4) and one subject receiving phenelzine plus amphetamine for treatment of depression (study 5). Integrated plasma activity for the 30-minute time period after injection is also presented.

| Study | Age | Region of interest | $K_i$ (milliliters of plasma per cubic centimeter of tissue per minute)* | | 30 min $\int_0^{} Cp(t)dt$ (nCi ml min) | |
|---|---|---|---|---|---|---|
| | | | [$^{11}$C] Clorgyline | L-[$^{11}$C] Deprenyl | [$^{11}$C] Clorgyline | L-[$^{11}$C] Deprenyl |
| 1 | 26 | Striatum | 0.21 | 0.44 | 2329 | 1818 |
| | | Thalamus | 0.27 | 0.56 | | |
| | | Cortex | 0.16 | 0.29 | | |
| | | Brainstem | 0.20 | 0.41 | | |
| 2 | 34 | Striatum | | 0.45 | 3206 | 2295 |
| | | Thalamus | | 0.51 | | |
| | | Cortex | | 0.28 | | |
| — | | Brainstem | | 0.41 | | |
| 3 | 39 | Striatum | 0.18 | 0.71 | 3260 | 1018 |
| | | Thalamus | 0.17 | 0.73 | | |
| | | Cortex | 0.16 | 0.54 | | |
| | | Brainstem | 0.17 | 0.47 | | |
| 4 | 86 | Striatum | 0.19 | 0.86 | 3611 | 1618 |
| | | Thalamus | 0.22 | 0.86 | | |
| | | Cortex | 0.12 | 0.53 | | |
| | | Brainstem | 0.15 | 0.64 | | |
| 5 | 72 | Striatum | 0.07 | 0.27 | 3965 | 2776 |
| | | Thalamus | 0.08 | 0.23 | | |
| | | Cortex | 0.04 | 0.10 | | |
| | | Brainstem | 0.06 | 0.23 | | |

Chromatography: Progress of the reactions was followed by high performance liquid chromatography using a C-18 reversed phase column (4.6×250 mm) and UV detection at 254 num. The solvent system for the deprenyl series was (70:30) methanol: 0.05 N ammonium formate; for the clorgyline series the ratio was 80:20. Flow in each case was 1 ml/min. Preparative scale purification was achieved by conventional liquid column chromatography (12 cm×5 cm) using silica gel 60 (230×400 mesh) (Merck). The content of the column eluent fractions was monitored by thin layer chromatography using plastic plates precoated with silica gel 60F (Merck), the plates being developed with the same solvent as had been used to eluate the column.

EXAMPLE 2

Preparation of 3-(2,4-Dichlorophenoxy)propylbromide 2,4-Dichlorophenol (20.5 g, 0.126 mol), 1,3-dibromopropane (49.1 g, 0.243 mol) and a solution of 5 g NaOH in 20 ml H$_2$O were refluxed for 75 min (oil bath 135°). A solution of 4.5 g of NaOH in 32 ml H$_2$O was added and the mixture was heated on a steam bath for 1½ hr. The layers were separated, the organic layer was extracted with water and then subjected to vacuum distillation (3–4 mm). A 19.6 g forecut was collected from room temperature to 50°. The product (20.5 g, 57%) distilled from 134°–137°. HPLC analysis (MeOH: 0.05N NH$_4$HCO$_2$ 80:20) showed the material to be 87% pure. Retention times of the impurities were 4.8 and 8.8 min while the product was 11.6 min. Extraction with water had no effect on the composition. As the impurities were found to be inert during the subsequent reactions, the material was used without further purification.

EXAMPLE 3

General Procedure for the Reaction of Amines with Alkyl Bromines

To a solution containing 11 mmole of alkyl bromide and 22 mmole of amine in 30 ml of acetonitrile was added a solution of 12 mmole K$_2$CO$_3$ in 3 ml of H$_2$O. The resulting clear two phase mixture was stirred at room temperature until HPLC analysis demonstrated that all of the alkyl bromide had been consumed. During this time precipitated KBr had caused the aqueous layer to thicken to a gummy solid. The acetronitrile was decanted, treated with fresh K$_2$CO$_3$, filtered and evaporated on a rotary evaporator. Absolute ethanol was added to the residue and evaporated. The residue, which consisted of a yellow to brown free flowing liquid and a fine white solid, was treated with a minimum volume of ethyl ether sufficient to disolve the liquid and this solution was applied to the silica gel column. After a forecut was collected, 10 ml fractions of a column eluate were taken. The fractions containing the desired product, as determined by tlc, were combined and evaporated to give the alkylated amine as the free base.

EXAMPLE 4

Preparation of N-[3-(2,4-Dichlorophenoxyl)propyl]-2-propynyl amine (norclorgyline)

2.3 ml of 87% pure 3-(2,4-dichlorophenoxyl) propylbromide (2.99 g; 0.011 mole) and 1.6 ml propargylamine (1.38 g; 0.025 mole) in 30 ml CH$_3$CN and 1.65 g k$_2$CO$_3$ in 3 ml H$_2$O were stirred at room temperature for 5 days.

HPLC retention time (min) norclorgyline 5.8.

Norclorgyline eluted from the silica column in 200–320 ml of ether.

Yield 1.5g (30%). mp hydrochloride salt 145°–147°.

EXAMPLE 5

Preparation of N-[3-(2,4-Dichlorophenoxyl]-N-methyl-2-propynylamine (clorgyline)

2.9 g of 87% 3-(2,4-dichlorophenoxyl) propyl bromide and 2.0 ml N-methylpropargylamine (1.64 g; 0.024 mole) were treated as above. The reaction mixture was stirred for 2 days.

Clorgyline eluted in 110–180 ml.

HPLC retention time (min): clorgyline 8.4

Yield 1.8 g (76%). mp hydrochloride salt 97°–99°.

EXAMPLE 6

Preparation of l-α-Methyl-N-2-propynyl phenethylamine (Nordeprenyl)

A mixture of l-amphetamine (2.9 g, 0.022 mol) and propargyl bromide (80% in toluene; 1.3 g, 0.011 mol) in 30 ml CH$_3$CN and 1.65 g K$_2$CO$_3$ in 3 ml H$_2$O was stirred overnight.

HPLC retention times (min): propargyl bromide 3.8, toluene 8.7, amphetamine 4.4, nordeprenyl 5.6, and a second product presumed to be the dipropargylated amphetamine 9.3.

Care was taken when evaporating solutions of nordeprenyl in light of the volatility of deprenyl.

The eluting solvent for the silica column was ether; hexane 1:1. Nordeprenyl eluted in fractions 180–290 ml. Yield 1.37 g (72%) Mp (hydrochloride salt 158°14 160°).

D-Amphetamine and L-amphetamine were converted to the N-formyl-1-phenyl-2-amino-propanes according to the procedure of Cavallits and Grey (U.S. Pat. No. 3,489,840) and reduced to the corresponding N-α-dimethylphenethylamines with LiAlH$_4$.

L-N,α-Dimethylphenethylamine mp 168°–171°.

D-N,α-Dimethylphenethyl amine mp 167°–69°.

EXAMPLE 7

Preparation of D- and L-Deprenyl

To a solution of N,α-dimethylphenethylamine (1.9 g; 12.8 mmole) and propargyl bromide (1.52 g; 12.8 mmole) in 30 ml of acetonitrile was added a solution of 12 mmole of K$_2$CO$_3$ in 3 ml of H$_2$O and the mixture was stirred at room temperature for 1½ hours. The organic layer was decanted and then acidified with concentrated HCl. The solvent was evaporated and the residue taken up in 1N HCl. This solution was extracted with ether, which was discarded, then made basic with 10N NaOH and extracted again with ether. This ether layer was extracted with 1N HCl. The HCl was evaporated. Absolute ethanol was added to the residue and evaporated. The residue was dissolved in a mininum volume of absolute ethanol. Ethyl ether was added to this solution until crystallization occurred. Yield 1.8 g (63%).

L-Deprenyl mp 141°–142.5°.

D-Deprenyl mp 137.5–139.

EXAMPLE 8

Preparation of [$^{11}$C]Clorgyline

[$^{11}$C]O$_2$ is collected in 0.2 ml of a 1M LiAlH$_4$ solution and the solvent is then removed by a nitrogen flow. To the residue is added 0.5 ml of 57% HI solution and the mixture is heated at 170° for 5 minutes under nitrogen flow which carries the [$^{11}$C]H$_3$I which is produced into a solution of norclorgyline 2 mg in 0.2 ml of dimethylformamide+0.050 ml of DMSO plus 0.3 ml of CH$_3$CN cooled to −10° C. After trapping is complete the reaction vessel is heated at 135° for 5 minutes. The mixture is cooled, 0.5 ml of water is added and the entire solution is injected onto an HPLC column (ODS-1, 5 micron, 10 cm×250 cm) and the product is eluted with CH$_3$OH:0.05N NH$_4$HCO$_2$ (80:20) at a flow rate of 6 ml/min. The product elutes at 12–13 minutes and the elution volume is 6 ml. To the product is added 2 ml of 2% HCl (conc) in ethanol and the entire solution is evaporated to dryness. To the residue is added 3 ml of a 3:1 mixture of saline (USP, isotonic) and water (USP) and the solution is filtered through a 0.22 μm millipore filter into a sterilized multiinjection vial containing 0.1 ml of 1M NaHCO$_3$ (USP).

EXAMPLE 9

Preparation of [$^{11}$C]-L-deprenyl

[$^{11}$C]O$_2$ is collected in 0.2 ml of a 1M LiAlH$_4$ solution and the solvent is then removed by a nitrogen flow. To the residue is added 0.5 ml of 57% HI solution and the mixture is heated at 170° for 5 minutes under nitrogen flow which carries the [$^{11}$C]H$_3$I which is produced into a solution of nordeprenyl 10 mg in 0.2 ml of dimethylformamide+0.050 ml of DMSO plus 0.3 ml of CH$_3$CN cooled to −10° C. After trapping is complete the reaction vessel is heated at 135° C. for 5 minutes. The mixture is cooled, 0.5 ml of water is added and the entire solution is injected onto an HPLC column (ODS-1, 5 micron, 10 cm×250 cm) and the product is eluted with CH$_3$OH:0.05N NH$_4$HCO$_2$ (70:30) at a flow rate of 6 ml/min. The product elutes at 10–11 minutes and the elution volume is 5 ml. To the product is added 2 ml of 2% HCl (conc) in ethanol and the entire solution is evaporated to dryness. To the residue is added 3 ml of a 3:1 mixture of saline (USP, isotonic) and water (USP) and the solution is filtered through a 0.22 μm millipore filter into a sterilized multiinjection vial containing 0.1 ml of 1M NaHCO$_3$ (USP).

EXAMPLE 10

Preparation of [$^{11}$C]-Clorgyline, [$^{11}$C]-L-Deprenyl, and [$^{11}$C]-D-Deprenyl

[$^{11}$C]O$_2$ was converted to [$^{11}$C]methanol by purging through 0.2 ml of 1M LiAlH$_4$ in tetrahydrofuran (THF). When the trapping was complete the mixture was heated and the THF was evaporated with a stream of N$_2$. To the residue was added 0.5 ml 58% HI. The vessel was closed and heated to 160° under reflux. After a vigorous reflux had been established the vessel was opened to a stream of N$_2$ which carried the [$^{11}$C]methyl iodide into a cooled solution of 0.3 ml of CH$_3$CN and 0.2 ml of a mixture of DMF:DMSO (4:1) containing the appropriate desmethyl precursor (free base) at −40°. For clorgyline 2 μl of the free base was used and for L-deprenyl and D-deprenyl 10 μl of the free base was used. The solution was heated in the closed vessel to 125° for 5 minutes. Then 0.5 ml of water was added and the solution injected onto a C-18 preparative HPLC column (Spherisorb ODS 2, 10×250 nm). For [$^{11}$C]clorgyline the solvent was MeOH: 0.05N NH$_4$HCO$_2$, 80:20, flow 5 ml/min, retention time 9 min. For [$^{11}$C]-L- and D-deprenyl the solvent was MeOH: 0.05N NH$_4$HCO$_2$, 70:30; flow 5 ml/min retention time 11 min. The fraction containing the product was evaporated in the presence of 2 ml of 2% HCl (conc) in ethanol. To the residue was added 2 ml EtOH and this was evaporated. The residue was dissolved in 3 ml saline:H$_2$O (3:1) and 0.3 ml was retained for HPLC analysis and determination of specific activity. The remainder of the solution was passed through a 22 μm millipore filter into a vial containing 0.1 ml of 1M NaHCO$_3$.

The radiochemical yields were 25–40% with a synthesis time of 35 minutes. The specific activities were about 0.8–2.0 Ci μmol$^{-1}$ at EOB.

EXAMPLE 11

Male Swiss albino mice (Brookhaven National Laboratory, Upton, N.Y., strain) were injected intravenously with 100–200 μCi of [$^{11}$C]clorgyline and [$^{11}$C]-L-deprenyl and killed by cervical fracture at 5, 30 and 60 min. post injection. Organs were rapidly removed, blotted free of blood, placed in preweighed counting vials, and counted, along with injection standards, in a sodium iodide well counter.

For the determination of protein binding, freshly excised brains were minced in preweighed centrifuge tubes containing 2 ml 0.4% HClO$_4$ (0.4M), weighed, counted, diluted with 1 ml HClO$_4$ and 1 ml methanol, and homogenized by ultrasonication. After centrifugation and decantation, the pellets were resuspended in 3 ml methanol, sonicated, and recentrifuged. The combined supernatants and pellet were counted in a sodium iodide well counter. Recovery in the supernatant was >90%. Because of the short half-life of C-11, corrections for the decay of the isotope were calculated to a standard time (end of cyclotron bombardment) for all data.

For pretreatment experiments, mice were given intraperitoneal injections of unlabeled clorgyline or L-deprenyl (10 mg/kg) one hour before the administration of the [$^{11}$C]-tracer. For example, clorgyline was followed by [$^{11}$C]clorgyline (pretreatment) or by [$^{11}$C]-L-deprenyl (cross pretreatment).

The tissue distribution and clearance patterns of [$^{11}$C]clorgyline are summarized in FIG. 1a, while those of [$^{11}$C]-L-deprenyl are given in FIG. 1b. Also shown is the effect of pretreatment with the unlabeled compound. In two separate studies of cross inhibition ([$^{11}$C]clorgyline pretreated with L-deprenyl and [$^{11}$C]-L-deprenyl pretreated with clorgyline) the patterns of uptake and clearance of radioactivity were, for the most part, similar to those observed in the control study.

Figure 2:
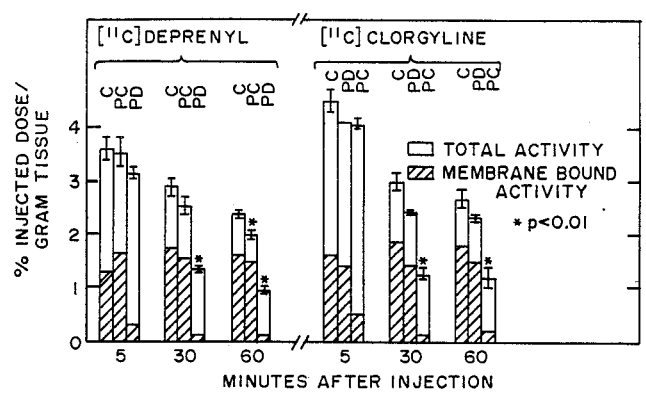
FIG. 2 shows the time course of radioactivity in the brain of control mice (C) and those pretreated with clorgyline (PC) or L-deprenyl (PD). Open bars: total activity (average±S.E.M. of 4 to 8 animals). Hatched bars: activity bound to membranes.

The fraction of membrane bound radioactivity in brains in control, pretreated and cross pretreated mice are given in FIG. 2.

As seen in FIG. 1, the biodistribution of [$^{11}$C]clorgyline and [$^{11}$C]-L-deprenyl is specifically associated with the presence of metabolically active MAO subtypes. The clearance patterns of [$^{11}$C]clorgyline and [$^{11}$C]-L-deprenyl differ in some organs of control animals. The retention of L-deprenyl in heart contrasts with the clearance of clorgyline from this organ with a similar, although less dramatic pattern being observed for lung. After pretreatment with L-deprenyl, these organs clear

[$^{11}$C]clorgyline, suggesting that MAO-B is the principal MAO subtype in mouse heart and lung. The results for liver, which is also predominantly type B, appear to be nonspecific.

In brain, [$^{11}$C]clorgyline and [$^{11}$C]-L-deprenyl display similar patterns to each other in both control and pretreated mice, with clorgyline concentration in the cerebral region and with clorgyline showing a slight but consistently higher uptake than L-deprenyl, indicating the comparable presence of MAO A and B in mouse brain. As can be seen from FIG. 2, the effect of pretreatment was a specific one in that cross pretreatment, e.g., clorgyline administration prior to [$^{11}$C]-L-deprenyl and L-deprenyl pretreatment prior to [$^{11}$C]clorgyline, did not significantly alter from control the patterns of [$^{11}$C]-L-deprenyl or [$^{11}$C]clorgyline disposition, respectively. Furthermore, the specificity of the inhibition of membrane binding in brain of [$^{11}$C]clorgyline and [$^{11}$C]-L-deprenyl by pretreatment relative to control animals is even more dramatic (see FIG. 2) indicating that covalent binding and probably suicide inhibition of monoamine oxidase are responsible for the pattern of radioactivity distribution observed in brain. The results of these pretreatment and cross pretreatment experiments support the premise of specific binding in vivo of [$^{11}$C]clorgyline to MAO A and [$^{11}$C]-L-deprenyl to MAO B.

We claim:

1. A method of selective irreversible binding and mapping of functional monoamine oxidase activity in vivo in different body tissues and organs using positron emission tomography which comprises administering an effective amount of the radiotracers [$^{11}$C]clorgyline of the formula N-[3-(2,4-dichlorophenoxyl)propyl]-N—$^{11}$CH$_3$-2-propynylamine which binds irreversibly to monoamine oxidase-A, and [$^{11}$C]-L-deprenyl of the formula N,α-CH$_3$—N- CH$_3$—N-2-propynylphenethylamine, which binds irreversibly to monoamine oxidase-B, prior to performing the positron emission tomography.

2. The method of claim 1 wherein the radiotracer [$^{11}$C]clorgyline is used for mapping monoamine oxidase-A activity in the brain.

3. The method of claim 1 wherein the radiotracer [$^{11}$C]-L-deprenyl is used for mapping monoamine oxidase-B activity in the brain outside the cerebral area and in other body tissues and organs.

4. A method of mapping the presence of monoamine oxidase-A bound by [$^{11}$C]clorgyline and monoamine oxidase-B bound by [$^{11}$C]-L-deprenyl using positron emission tomography which comprises in vivo administration of an effective amount of [$^{11}$C]clorgyline of the formula N-[3-(2,4-dichlorophenoxyl)propyl]-N—$^{11}$CH$_3$-2-propynylamine or [$^{11}$C]-L-deprenyl of the formula N,α-CH$_3$—N—$^{11}$CH$_3$—N-2-propynylphenethylamine or both compounds together to produce an image of functional enzyme activity resulting from covalent binding of the radiotracers to the respective monoamine oxidase types.

5. The method of claim 4 wherein the monoamine oxidase-A bound by [$^{11}$C]clorgyline is present in the brain and non-brain tissue.

6. The method of claim 4 wherein the monoamine oxidase-B which is bound by [$^{11}$C]-L-deprenyl is present principally in the non-cerebral portion of the brain and in non-brain tissues.

7. [$^{11}$C]clorgyline of the formula N-[3-(2,4-dichlorophenoxyl)propyl]-N—$^{11}$CH$_3$-2-propynylamine.

8. [$^{11}$C]-L-deprenyl of the formula N,α-CH$_3$—N—$^{11}$CH$_3$—N-2-propynylphenethylamine.

* * * * *